(12) United States Patent
Eggeling et al.

(10) Patent No.: US 7,632,663 B1
(45) Date of Patent: Dec. 15, 2009

(54) METHOD FOR MICROBIALLY PRODUCING L-VALINE (75) Inventors: Lothar Eggeling, Jülich (DE); Hermann Sahm, Jülich (DE)

(73) Assignee: Forschungszentrum Julich GmbH (DE)

( * ) Notice: Subject to any disclaimer, the term of this patent is extended or adjusted under 35 U.S.C. 154(b) by 0 days.

(21) Appl. No.: 09/914,006

(22) PCT Filed: Feb. 21, 2000

(86) PCT No.: PCT/EP00/01405

§ 371 (c)(1), (2), (4) Date: Jan. 7, 2002

(87) PCT Pub. No.: WO00/50624

PCT Pub. Date: Aug. 31, 2000

(30) Foreign Application Priority Data

Feb. 22, 1999 (DE) .................................. 199 07 567

(51) Int. Cl.
C12P 13/04 (2006.01)
C12N 9/02 (2006.01)
C12N 9/04 (2006.01)
C12N 9/10 (2006.01)
C12N 9/88 (2006.01)
C12N 15/00 (2006.01)

(52) U.S. Cl. ...................... 435/106; 435/189; 435/190; 435/193; 435/232; 435/320.1; 536/23.1

(58) Field of Classification Search ................. 435/106, 435/189, 190, 193, 232, 320.01; 536/23.1
See application file for complete search history.

(56) References Cited

U.S. PATENT DOCUMENTS

| 4,278,765 A | 7/1981 | Debabov et al. |
| 5,658,766 A | 8/1997 | Livshits et al. |

FOREIGN PATENT DOCUMENTS

| EP | 0136359 | 4/1985 |
| EP | 0 136 359 | 10/1985 |
| EP | 0 356 739 | 3/1990 |
| EP | 0356739 | 3/1990 |
| EP | 0356739 A1 * | 3/1990 |
| EP | 0 872 547 | 10/1998 |
| EP | 0872547 | 10/1998 |
| JP | 06/277067 | 10/1994 |
| JP | 08-089249 | 4/1996 |
| JP | 08089249 A2 * | 4/1996 |

OTHER PUBLICATIONS

Reuter. Genetic and physiological analysis of the formation of pantothenate and valine in *Corynebacterium glutamicum*. Berichte des Forschungszentrums Juelich (1998), Juel-3606, 1-115 pp. (Abstract).*

Zhou et al. Protein Expr Purif. Mar. 2004;34(1):87-94.*
Keilhauer et al. J Bacteriol. Sep. 1993;175(17):5595-603.*
SEQ ID No. 1 Alignment to SEQ ID No. 4 of US Patent 6,177,264.*
Lawther, R. P., et al., "The Complete Nucleotide Sequence of the ilvGMEDA Operon of *Escherichia coli* K-12," *Nucleic Acids Research* 15:2137-2155, XP-002138603 (1987).
Miller, S. L., et al., "Prebiotic syntheses of vitamin coenzymes: II. Pantoic acid, pantothenic acids, and the composition of coenzyme A," *J. of Molecular Evolution* 36: 308-314, XP-002138606 (1993).
Keilhauer, C., et al., "Isoleucine Synthesis in *Corynebacterium glutamicum*: Molecular Analysis of the ilvB-ilvN-ilvC Operon," *J. of Bacteriology* 175:5595-5603, XP000611312 (1993).
Sahm, H, et al., "D-Pantothenate Synthesis in *Corynebacterium glutamicum* and use of panBC and Genes Encoding L-Valine Synthesis for D-Pantothenate Overproduction," *Applied and Environmental Microbiology* 65:1973-1979, XP-002138605 (1999).
Velasco, Juan A., et al., "Cloning of the dihydroxyacid de-hydratase-encoding gene (ILV3) from *Saccharomyces cerevisiae*," *Gene* (Amsterdam) 137:179-185, XP-002138604 (1993).
R. P. Lawther et al; "The complete nucleotide sequence of the ilvGMEDA operon of *Escherichia coli* K-12"; Nucleic Acids Research; vol. 15, No. 5, 1987; pp. 2137-2155.
S. L. Miller; "Prebiotic syntheses of vitamin coenzymes" Journal of Molecular Evolution; vol. 36; 1993; pp. 308-314 (Abstract).
C. Keilhauer; "Isoleucine Synthesis of Corynebacterium glutamicum: Moluelar Analysis of the ilvB-ilvN-ilvC Operon"; Jounal of Bacteriology; Sep. 1993; vol. 175, pp. 5595-5603.
H. Sahm; "D-Pantothenate Synthesis in Corynebacterium glutamicum and Use of panBC and Genes Encoding L-Valine Synthesis for D-Pantothenate Overproduction"; Applied and Environmental Microbiology; May 1999; vol. 65, pp. 1973-1979.
J. A. Velasco: "Cloning of the dihydroxyacid dehydratase-encoding gene (ILV3) from *Saccharomyces cerevisiae*"; Gene; 1993; vol. 137, pp. 179-185.
L. Gusberti et al., "Cloning and Sequencing of the ilv BNC gene cluster from *Mycobacterium avium*", Gene, vol. 177, pp. 83-85, 1996.
E. De Rossi et al., "Cloning, Sequencing and Expression of the ilv BNC Gene Cluster from *Streptomyces avermitilis*", Gene, vol. 166, pp. 127-132, 1995.
J. A. Velasco et al. "Cloning of the dihydroxyacid dehydratase-encoding gene (*ILV3*) from *Saccharomyces cerevisiae*," Gene 137: 179-185, 1993.

(Continued)

*Primary Examiner*—Christian L Fronda
(74) *Attorney, Agent, or Firm*—Connolly Bove Lodge & Hutz LLP (57) ABSTRACT

The present invention relates to a process for the microbial production of L-valine in which the dihydroxy acid-synthase (ilvD) activity and/or the ilvD gene expression is intensified in a microorganism. As an alternative or in combination with this, the acetohydroxy acid-synthase (ilvBN) activity and isomeroreductase (ilvC) activity and/or the ilvBNC gene expression are intensified in a microorganism. The process according to the invention preferably makes use of microorganisms in which the activity of at least one enzyme that is involved in a metabolic pathway that reduces the formation of L-valine is weakened or eliminated. Thus, for instance, the process according to the invention preferably makes use of microorganisms having a defect mutation in the threonine dehydratase (ilvA) gene and/or a defect mutation in one or more genes of the pantothenate synthesis.

23 Claims, 3 Drawing Sheets

OTHER PUBLICATIONS

Billman-Jacobe, H., et al., "Expression and Secretion of Heterologous Proteases by *Corynebacterium glutamicum*", Applied and Environmental Microbiology, Apr. 1995, vol. 61, No. 4, pp. 1610-1613.

Menkel, E., et al, "Influence of Increased Aspartate Availablity on Lysine Formation by a Recombinant Strain of *Corynebacterium glutamicum* and Utilization of Fumarate", Applied and Environmental Microbiology, Mar. 1989, vol. 55, No. 3, pp. 684-688.

* cited by examiner

SEQUENCE LISTING

<160> NUMBER OF SEQ ID NOS: 7

<210> SEQ ID NO 1
<211> LENGTH: 2952
<212> TYPE: DNA
<213> ORGANISM: Corynebacterium glutamicum

<400> SEQUENCE: 1

```
agtacttgga gcgccaaaag gcactgggca agccagttca gttgaacttc gatgacgaca      60
ccgatgggaa tacaacacaa acagaaagcg ttgaatccca agagaccgga caagccgcgt     120
ctgaaacctc acatcgtgat aaccctgcgt cacagcacta gagtgtaata agccgtccga     180
accaaaggtc cacacctctg cacgagtaga agctcaccca agttttcaaa gtgccgttga     240
ttcttgacaa ccacccgccg ctctttagag cagatttgaa aagcgcatca tgatcccact     300
tcgttcaaaa gtcaccaccg tcggtcgcaa tgcagctggc gctcgcgccc tttggcgtgc     360
caccggcacc aaggaaaatg agttcggcaa gccaattgtt gccatcgtaa actcctacac     420
ccagttcgtg cccggacacg ttcaccttaa gaacgtcggc gatattgtgg cagatgcagt     480
gcgcaaagcc ggtggcgttc caaaggaatt caacaccatc gtcgatgacg gcatcgccat     540
gggacacggc ggcatgctgt actccctgcc atcccgtgaa atcatcgccg actccgtcga     600
atacatggtc aacgcacaca ccgccgacgc catggtgtgt atctccaact gtgacaagat     660 cacccccaggc atgctcaacg cagcaatgcg cctgaacatc ccagtggtct tcgtttccgg     720
tggcccaatg gaagctggca aggctgtcgt cgttgagcgc gttgcacacg caccaaccga     780
cctcatcacc gcgatctccg catccgcaag cgatgcagtc gacgacgcag gccttgcagc     840
cgttgaacga tccgcatgcc caacctgtgg ctcctgctcc ggtatgttca ccgcgaactc     900
catgaactgc ctcaccgaag ctctgggact ttctctcccg ggcaacggct ccactctggc     960
aacccacgca gcacgtcgcg cactgtttga aaaggccggc gaaaccgtcg ttgaactgtg    1020
ccgccgctac tacggtgaag aagacgaatc cgttctgcca cgtggcattg ccaccaagaa    1080
ggcattcgaa aacgcaatgg cactggatat ggccatgggt ggatccacca acaccatcct    1140
ccacatcctc gcagctgccc aggaaggcga agttgacttc gacctcgcag acatcgacga    1200
actgtccaaa aacgtcccct gcctgtccaa ggttgcacca aactccgact accacatgga    1260
agacgtccac cgcgccggtc gcattccagc actgctcggc gagctcaacc gcggtggcct    1320
gctgaacaag gacgtccact ccgttcactc caacgacctt gaaggttggt tggatgactg    1380
ggatatccgc tctggcaaga ccaccgaagt agcaaccgaa ctcttccacg cagccccagg    1440
tggcatccgc accaccgaag cattctccac cgagaaccgc tgggacgaac tcgacaccga    1500
cgctgccaag ggctgcatcc gcgacgttga acacgcctac accgccgacg gcggcctggt    1560
```

-continued

```
tgttcttcgc ggcaacatct cccctgacgg cgcagtgatc aagtccgcag gtatcgaaga   1620
agagctgtgg aacttcaccg gaccagcacg agttgtcgaa agccaggaag aggcagtctc   1680
tgtcatcctg accaagacca tccaagctgg cgaagttctg gtcgtccgct acgaaggccc   1740
atcaggtgga ccaggcatgc aggaaatgct tcacccaacc gcattcctca agggatccgg   1800
cctgggcaag aagtgtgcac tgatcaccga cggccgtttc tccggaggtt cctcaggact   1860
gtccatcggc cacgtctccc cagaagcagc acacggcgga gtcattggtc tgatcgaaaa   1920
cggcgacatc gtctccatcg acgttcacaa ccgcaagctc gaagttcagg tctccgacga   1980
ggaactccag cgccgccgcg acgctatgaa cgcctccgag aagccatggc agccagtcaa   2040
ccgtaaccgc gttgtcacca aggcactgcg cgcatacgca agatggcta cctccgctga   2100 taagggtgca gtccgtcagg tcgactaacc ctttgtgagt gtttgagcac cggttcccta   2160
ctttgggttc cggtgctttt tcatgtcttg gcctgtgtgg gcgtggtgga gctcccgtt    2220 gcaaatactc accacaagtt gcaggatttc tgctggttgt ggtggatttt cccgctttat   2280
agccctatgc gtgcaacttt cggaccgatt ccaaagggca agccctgtt tgtggtggat    2340 ccttgccctg gaagctttca ggaaccacaa ctaccccact gaccccaaag tggataggcc   2400
ctattcttcc gtttaagcgc ctcaaacacc tctccccaca cttgacccat taggcaatta   2460
cgaatcctta aacagccttc tacagcacca tgccccaaac cgaacccagg catgaaaaag   2520
accctcacca ggagggtctt tttctaaaac tttggctacg cgattgggtt cacacccgca   2580
ccgaaccacc acagcagaac tgccgctgcg atgccgatga ccacgaagat ccacgagctc   2640
accagtggac gctttgccca acctcggcca gagtcaaggg aaatcttgcc ggggccggtg   2700
aactgaagtc cgacaaccac gatagtgagg atcagtgcca gcatcaatgg ctcactaagt   2760
tcaccccaac caccttcatg agtgttgact tggtgaaggg tggtaaagga tgtcgccacc   2820
gtggctaccg ctgctgccac tggggtcatc agaccaagga gcaggaagac accagccgca   2880
agttcaatag atggaagcag gatcgcgagg atttcaggcc actggtaacc agcgaactct   2940
gcctcgactc ta                                                       2952
```

<210> SEQ ID NO 2
<211> LENGTH: 612
<212> TYPE: PRT
<213> ORGANISM: Corynebacterium glutamicum

<400> SEQUENCE: 2

Met Ile Pro Leu Arg Ser Lys Val Thr Thr Val Gly Arg Asn Ala Ala
1               5                   10                  15

Gly Ala Arg Ala Leu Trp Arg Ala Thr Gly Thr Lys Glu Asn Glu Phe
            20                  25                  30

Gly Lys Pro Ile Val Ala Ile Val Asn Ser Tyr Thr Gln Phe Val Pro
        35                  40                  45

Gly His Val His Leu Lys Asn Val Gly Asp Ile Val Ala Asp Ala Val
    50                  55                  60

Arg Lys Ala Gly Gly Val Pro Lys Glu Phe Asn Thr Ile Val Asp Asp
65                  70                  75                  80

Gly Ile Ala Met Gly His Gly Met Leu Tyr Ser Leu Pro Ser Arg
            85                  90                  95

Glu Ile Ile Ala Asp Ser Val Glu Tyr Met Val Asn Ala His Thr Ala
            100                 105                 110

Asp Ala Met Val Cys Ile Ser Asn Cys Asp Lys Ile Thr Pro Gly Met
        115                 120                 125

```
Leu Asn Ala Ala Met Arg Leu Asn Ile Pro Val Val Phe Val Ser Gly
        130                 135                 140

Gly Pro Met Glu Ala Gly Lys Ala Val Val Val Glu Arg Val Ala His
145                 150                 155                 160

Ala Pro Thr Asp Leu Ile Thr Ala Ile Ser Ala Ser Ala Ser Asp Ala
                165                 170                 175

Val Asp Asp Ala Gly Leu Ala Ala Val Glu Arg Ser Ala Cys Pro Thr
            180                 185                 190

Cys Gly Ser Cys Ser Gly Met Phe Thr Ala Asn Ser Met Asn Cys Leu
        195                 200                 205

Thr Glu Ala Leu Gly Leu Ser Leu Pro Gly Asn Gly Ser Thr Leu Ala
    210                 215                 220

Thr His Ala Ala Arg Arg Ala Leu Phe Glu Lys Ala Gly Glu Thr Val
225                 230                 235                 240

Val Glu Leu Cys Arg Arg Tyr Tyr Gly Glu Glu Asp Glu Ser Val Leu
                245                 250                 255

Pro Arg Gly Ile Ala Thr Lys Lys Ala Phe Glu Asn Ala Met Ala Leu
            260                 265                 270

Asp Met Ala Met Gly Gly Ser Thr Asn Thr Ile Leu His Ile Leu Ala
        275                 280                 285

Ala Ala Gln Glu Gly Glu Val Asp Phe Asp Leu Ala Asp Ile Asp Glu
    290                 295                 300

Leu Ser Lys Asn Val Pro Cys Leu Ser Lys Val Ala Pro Asn Ser Asp
305                 310                 315                 320

Tyr His Met Glu Asp Val His Arg Ala Gly Arg Ile Pro Ala Leu Leu
                325                 330                 335

Gly Glu Leu Asn Arg Gly Gly Leu Leu Asn Lys Asp Val His Ser Val
            340                 345                 350

His Ser Asn Asp Leu Glu Gly Trp Leu Asp Asp Trp Asp Ile Arg Ser
        355                 360                 365

Gly Lys Thr Thr Glu Val Ala Thr Glu Leu Phe His Ala Ala Pro Gly
    370                 375                 380

Gly Ile Arg Thr Thr Glu Ala Phe Ser Thr Glu Asn Arg Trp Asp Glu
385                 390                 395                 400

Leu Asp Thr Asp Ala Ala Lys Gly Cys Ile Arg Asp Val Glu His Ala
                405                 410                 415

Tyr Thr Ala Asp Gly Gly Leu Val Val Leu Arg Gly Asn Ile Ser Pro
            420                 425                 430

Asp Gly Ala Val Ile Lys Ser Ala Gly Ile Glu Glu Glu Leu Trp Asn
        435                 440                 445

Phe Thr Gly Pro Ala Arg Val Val Glu Ser Gln Glu Glu Ala Val Ser
    450                 455                 460

Val Ile Leu Thr Lys Thr Ile Gln Ala Gly Glu Val Leu Val Val Arg
465                 470                 475                 480

Tyr Glu Gly Pro Ser Gly Gly Pro Gly Met Gln Glu Met Leu His Pro
                485                 490                 495

Thr Ala Phe Leu Lys Gly Ser Gly Leu Gly Lys Lys Cys Ala Leu Ile
            500                 505                 510

Thr Asp Gly Arg Phe Ser Gly Gly Ser Ser Gly Leu Ser Ile Gly His
        515                 520                 525

Val Ser Pro Glu Ala Ala His Gly Gly Val Ile Gly Leu Ile Glu Asn
    530                 535                 540
```

-continued

```
Gly Asp Ile Val Ser Ile Asp Val His Asn Arg Lys Leu Glu Val Gln
545                 550                 555                 560

Val Ser Asp Glu Glu Leu Gln Arg Arg Arg Asp Ala Met Asn Ala Ser
            565                 570                 575

Glu Lys Pro Trp Gln Pro Val Asn Arg Asn Arg Val Val Thr Lys Ala
        580                 585                 590

Leu Arg Ala Tyr Ala Lys Met Ala Thr Ser Ala Asp Lys Gly Ala Val
        595                 600                 605

Arg Gln Val Asp
    610
```

<210> SEQ ID NO 3
<211> LENGTH: 2164
<212> TYPE: DNA
<213> ORGANISM: Corynebacterium glutamicum

<400> SEQUENCE: 3

| | |
|---|---:|
| gcttcggggt accaattcct ttaagaacca tcagatcaat ctgttgtaca ttctcggcca | 60 |
| gattcagctt ttcggtaagg acgaaacact ttcacttgaa tcggcagcaa agtttcttaa | 120 |
| agtttctaag gcaactgcaa cgaggtattt tagaactctc cgagaaatgg aattagttca | 180 |
| cgaggtcagc aaacgccctt gcggtttgc gctcacggat aaaggtcgtg agatagtagg | 240 |
| tcttgaggta aaaatttgac tccataacga gaacttaatc gagcaacacc cctgaacagt | 300 |
| gaatcaaatc ggaattttat tattctgagc tggtcatcac atctatactc atgcccatgt | 360 |
| caggcattga tgcaaagaaa atccgcaccc gtcatttccg cgaagctaaa gtaaacggcc | 420 |
| agaaagtttc ggttctcacc agctatgatg cgctttcggc gcgcattttt gatgaggctg | 480 |
| gcgtcgatat gctccttgtt ggtgattccg ctgccaacgt tgtgctgggt cgcgatacca | 540 |
| ccttgtcgat caccttggat gagatgattg tgctggccaa gcggtgacg atcgctacga | 600 |
| agcgtgcgct tgtggtggtt gatctgccgt ttggtaccta tgaggtgagc ccaaatcagg | 660 |
| cggtggagtc cgcgatccgg gtcatgcgtg aaacgggtgc ggctgcggtg aagatcgagg | 720 |
| gtggcgtgga gatcgcgcag acgattcgac gcattgttga tgctggaatt ccggttgtcg | 780 |
| gcccacatcgg gtacaccccg cagtccgagc attccttggg cggccacgtg gttcagggtc | 840 |
| gtggcgcgag ttctggaaag ctcatcgccg atgcccgcg gttggagcag gcgggtgcgt | 900 |
| ttgcggttgt gttggagatg gttccagcag aggcagcgcg cgaggttacc gaggatcttt | 960 |
| ccatcaccac tatcggaatc ggtgccggca atggcacaga tgggcaggtt ttggtgtggc | 1020 |
| aggatgcctt cggcctcaac cgcggcaaga agccacgctt cgtccgcgag tacgccacct | 1080 |
| tgggcgattc cttgcacgac gccgcgcagg cctacatcgc cgatatccac gcgggtacct | 1140 |
| tcccaggcga agcggagtcc ttttaatgca ggtagcaacc acaaagcagg cgcttatcga | 1200 |
| cgccctcctc caccacaaat ccgtcgggct cgtccccacc atgggtgcgc tacacagcgg | 1260 |
| acacgcctcg ttggttaaag cagcacgcgc tgaaaacgac actgttgtag ccagtatttt | 1320 |
| tgtcaatccc ctgcagtttg aagcactcgg tgattgcgat gattaccgca actatccccg | 1380 |
| ccaactcgac gccgatttag cactgcttga agaggcaggt gtggatattg tgttcgcacc | 1440 |
| cgatgtggag gaaatgtacc ccggtggctt gccactagtg tgggcgcgca ccggttccat | 1500 |
| cggaacaaaa ttggagggtg ccagcaggcc tggccatttc gatggtgtgg ctaccgtggt | 1560 |
| ggcgaagctg ttcaatttgg tgcgccctga tcgtgcatat tttggacaaa agatgctca | 1620 |
| gcaggttgcg gtgattcggc gattggttgc cgatctagac attcccgtgg agattcgtcc | 1680 |

-continued

```
cgttccgatt attcgtggcg ccgatggctt agccgaatcc agccgcaatc aacgtctttc    1740
tgcggatcag cgagcgcaag ctctggtgct gccgcaggtg ttgagtgggt tgcagcgtcg    1800
aaaagcagct ggtgaagcgc tagatatcca aggtgcgcgc gacaccttgg ccagcgccga    1860
cggcgtgcgc ttggatcacc tggaaattgt cgatccagcc accctcgaac cattagaaat    1920
cgacggcctg ctcacccaac cagcgttggt ggtcggcgcg attttcgtgg ggccggtgcg    1980
gttgatcgac aatatcgagc tctagtacca accctgcgtt gcagcacgca gcttcgcata    2040
acgcgtgctc agctcagtgt ttttaggtgc gcggtgcgga tcggaaccgg gagttggcca    2100
ctgcggtggc gtggcctcac ccgacagcgc ccatgccgcc tgacgagctg cacccaacgc    2160
caca                                                                2164
```

<210> SEQ ID NO 4
<211> LENGTH: 271
<212> TYPE: PRT
<213> ORGANISM: Corynebacterium glutamicum

<400> SEQUENCE: 4

```
Met Pro Met Ser Gly Ile Asp Ala Lys Lys Ile Arg Thr Arg His Phe
1               5                   10                  15

Arg Glu Ala Lys Val Asn Gly Gln Lys Val Ser Val Leu Thr Ser Tyr
                20                  25                  30

Asp Ala Leu Ser Ala Arg Ile Phe Asp Glu Ala Gly Val Asp Met Leu
            35                  40                  45

Leu Val Gly Asp Ser Ala Ala Asn Val Val Leu Gly Arg Asp Thr Thr
        50                  55                  60

Leu Ser Ile Thr Leu Asp Glu Met Ile Val Leu Ala Lys Ala Val Thr
65                  70                  75                  80

Ile Ala Thr Lys Arg Ala Leu Val Val Asp Leu Pro Phe Gly Thr
                85                  90                  95

Tyr Glu Val Ser Pro Asn Gln Ala Val Glu Ser Ala Ile Arg Val Met
                100                 105                 110

Arg Glu Thr Gly Ala Ala Val Lys Ile Glu Gly Gly Val Glu Ile
            115                 120                 125

Ala Gln Thr Ile Arg Arg Ile Val Asp Ala Gly Ile Pro Val Val Gly
        130                 135                 140

His Ile Gly Tyr Thr Pro Gln Ser Glu His Ser Leu Gly Gly His Val
145                 150                 155                 160

Val Gln Gly Arg Gly Ala Ser Ser Gly Lys Leu Ile Ala Asp Ala Arg
                165                 170                 175

Ala Leu Glu Gln Ala Gly Ala Phe Ala Val Val Leu Glu Met Val Pro
            180                 185                 190

Ala Glu Ala Ala Arg Glu Val Thr Glu Asp Leu Ser Ile Thr Thr Ile
        195                 200                 205

Gly Ile Gly Ala Gly Asn Gly Thr Asp Gly Gln Val Leu Val Trp Gln
    210                 215                 220

Asp Ala Phe Gly Leu Asn Arg Gly Lys Lys Pro Arg Phe Val Arg Glu
225                 230                 235                 240

Tyr Ala Thr Leu Gly Asp Ser Leu His Asp Ala Ala Gln Ala Tyr Ile
                245                 250                 255

Ala Asp Ile His Ala Gly Thr Phe Pro Gly Glu Ala Glu Ser Phe
            260                 265                 270
```

<210> SEQ ID NO 5

```
<211> LENGTH: 279
<212> TYPE: PRT
<213> ORGANISM: Corynebacterium glutamicum

<400> SEQUENCE: 5

Met Gln Val Ala Thr Thr Lys Gln Ala Leu Ile Asp Ala Leu Leu His
1               5                   10                  15

His Lys Ser Val Gly Leu Val Pro Thr Met Gly Ala Leu His Ser Gly
            20                  25                  30

His Ala Ser Leu Val Lys Ala Ala Arg Ala Glu Asn Asp Thr Val Val
        35                  40                  45

Ala Ser Ile Phe Val Asn Pro Leu Gln Phe Glu Ala Leu Gly Asp Cys
    50                  55                  60

Asp Asp Tyr Arg Asn Tyr Pro Arg Gln Leu Asp Ala Asp Leu Ala Leu
65                  70                  75                  80

Leu Glu Glu Ala Gly Val Asp Ile Val Phe Ala Pro Asp Val Glu Glu
                85                  90                  95

Met Tyr Pro Gly Gly Leu Pro Leu Val Trp Ala Arg Thr Gly Ser Ile
            100                 105                 110

Gly Thr Lys Leu Glu Gly Ala Ser Arg Pro Gly His Phe Asp Gly Val
        115                 120                 125

Ala Thr Val Val Ala Lys Leu Phe Asn Leu Val Arg Pro Asp Arg Ala
    130                 135                 140

Tyr Phe Gly Gln Lys Asp Ala Gln Gln Val Ala Val Ile Arg Arg Leu
145                 150                 155                 160

Val Ala Asp Leu Asp Ile Pro Val Glu Ile Arg Pro Val Pro Ile Ile
                165                 170                 175

Arg Gly Ala Asp Gly Leu Ala Glu Ser Ser Arg Asn Gln Arg Leu Ser
            180                 185                 190

Ala Asp Gln Arg Ala Gln Ala Leu Val Leu Pro Gln Val Leu Ser Gly
        195                 200                 205

Leu Gln Arg Arg Lys Ala Ala Gly Glu Ala Leu Asp Ile Gln Gly Ala
    210                 215                 220

Arg Asp Thr Leu Ala Ser Ala Asp Gly Val Arg Leu Asp His Leu Glu
225                 230                 235                 240

Ile Val Asp Pro Ala Thr Leu Glu Pro Leu Glu Ile Asp Gly Leu Leu
                245                 250                 255

Thr Gln Pro Ala Leu Val Val Gly Ala Ile Phe Val Gly Pro Val Arg
            260                 265                 270

Leu Ile Asp Asn Ile Glu Leu
        275

<210> SEQ ID NO 6
<211> LENGTH: 26
<212> TYPE: DNA
<213> ORGANISM: Corynebacterium glutamicum

<400> SEQUENCE: 6
gagaacttaa tcgagcaaca cccctg                                        26

<210> SEQ ID NO 7
<211> LENGTH: 26
<212> TYPE: DNA
<213> ORGANISM: Corynebacterium glutamicum

<400> SEQUENCE: 7
gcgccacgcc tagccttggc cctcaa                                        26
```

METHOD FOR MICROBIALLY PRODUCING L-VALINE

The present invention relates to a process for the microbial production of L-valine according to claims 1 through 13 as well as to transformed cells or microorganisms according to claims 14 through 17 that can be employed in the process.

The amino acid L-valine is a commercially significant product that is used in animal and human nutrition as well as in medicine. Consequently, there is widespread interest in the creation of improved processes for the production of L-valine.

Valine can be manufactured by means of chemical synthesis or else by means of biotechnological methods by fermenting suitable microorganisms in the appropriate nutrient solutions. The advantage of producing microorganisms by means of biotechnology lies in the formation of the correct stereoisomeric form, namely the L-form of valine that is free of D-valine.

Various types of bacteria such as, for instance, *Escherichia coli, Serratia marcescens, Corynebacterium glutamicum, Brevibacterium flavum* or *Brevibacterium lactofermentum* can produce L-valine when in a nutrient solution that contains glucose. U.S. Pat. No. 5,658,766 shows that, in the case of *Escherichia coli*, an increased formation of L-valine can be achieved through mutation in the aminoacyl-tRNA-synthetase. WO 96 06926 also shows that an increase in the formation of L-valine can be achieved with *Escherichia coli* by means of a liponic acid auxotrophy. EP 0,694,614 A1 describes strains of *Escherichia coli* that are resistant to α-ketobutyric acid and that produce L-valine, L-isoleucine or L-leucine when in a nutrient solution that contains glucose.

EP 0,477,000 discloses that the formation of L-valine can be improved through the mutagenesis of *Corynebacterium* or *Brevibacterium* and through selection for valine resistance. The same European patent specification also reveals that improved L-valine formation can be achieved by selecting *Corynebacterium* or *Brevibacterium* for resistance to various pyruvate analogs, such as β-fluoropyruvate, β-chloropyruvate, β-mercaptopyruvate or trimethyl pyruvate. It is known from Nakayama et al. (Nakayama et al., 1961, J. Gen. Appl. Microbiol. Jpn.) that auxotrophies introduced by means of random mutations can lead to an improved L-valine accumulation.

Figure 1:
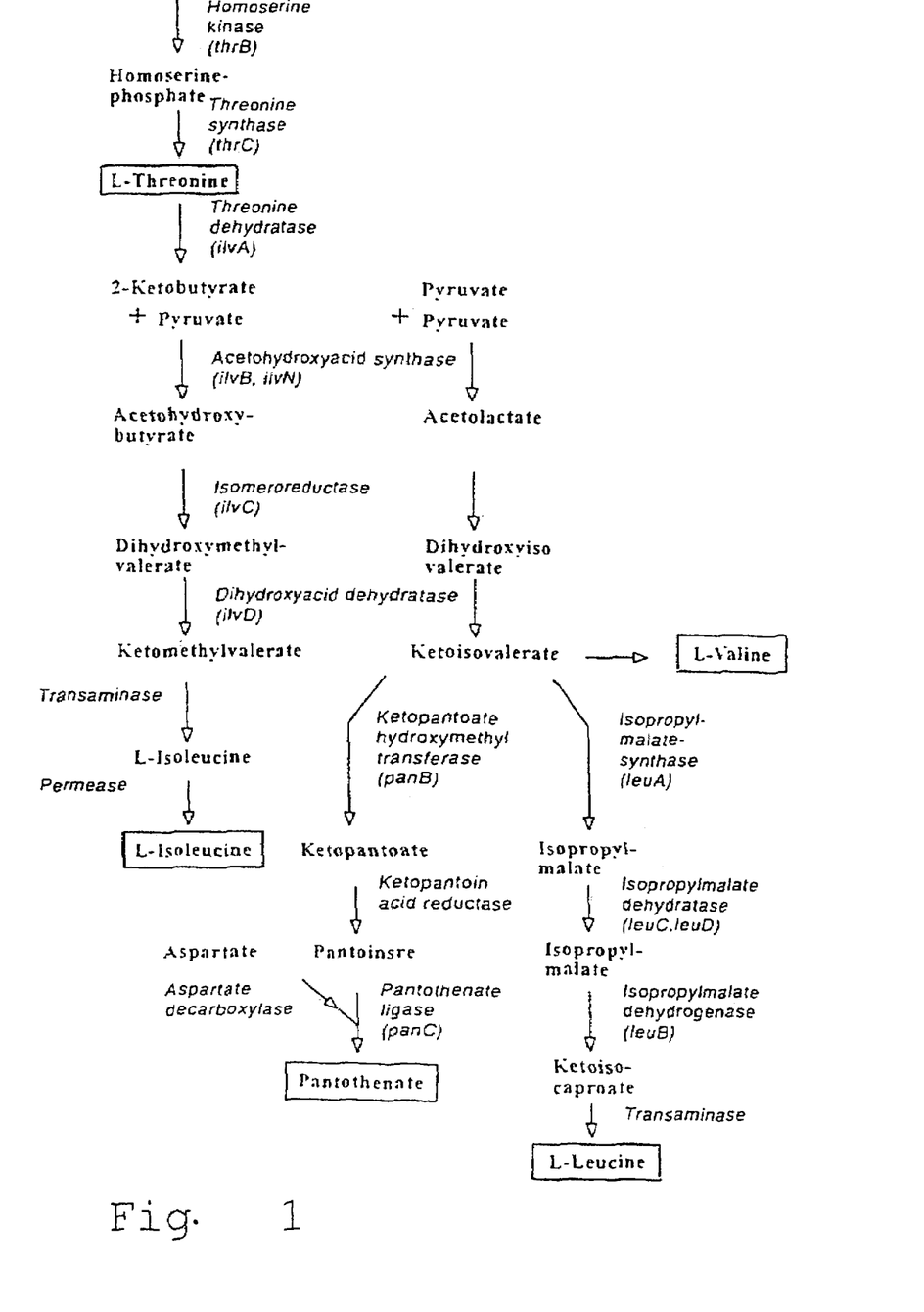
FIG. 1 shows a metabolic pathway for synthesis of L-valine, L-isoleucine, L-leucine and pantothenate.

Moreover, EP 0,356,739 A1 shows that the formation of L-valine is improved by means of the plasmid pAJ220V3 with the amplification of the DNA range that codes for the acetohydroxy acid-synthase (ilvBN, also see FIG. 1).

The present invention has the objective of providing new principles for the microbial production of L-valine, particularly by means of coryneform bacteria.

This objective is achieved according to the invention in that the dihydroxy acid-dehydratase (ilvD) activity and/or the ilvD gene expression are intensified in a micro-organism. As an alternative or in combination with this, the acetohydroxy acid-synthase (ilvBN) activity and isomeroreductase (ilvC) activity and/or the ilvBNC gene expression are intensified in a microorganism. The process according to the invention can additionally make use of microorganisms in which the activity of at least one enzyme involved in a metabolic pathway that reduces the formation of L-valine is weakened or eliminated. Thus, for instance, the process according to the invention preferably makes use of microorganisms having a defect mutation in the threonine dehydratase (ilvA) gene and/or a defect mutation in one or more genes of the pantothenate synthesis.

As defined in the invention being claimed, the terms "valine" or "L-valine" refer not only to the free acids but also to the salt thereof such as, for example, the calcium, sodium, ammonium or potassium salt.

The term "intensification" describes the increase in the intracellular activity of the cited enzymes ilvD, ilvB, ilvN and ilvC. In order to increase the enzyme activity, especially the endogenous activity in the microorganism is raised. An increase in the enzyme activity can be attained, for example, by changing the catalytic center so as to increase the substrate conversion or by eliminating the effect of enzyme inhibitors. Increased enzyme activity can also be brought about by increasing the enzyme synthesis, for example, by means of gene amplification or by eliminating factors that repress enzyme biosynthesis. According to the invention, the endogenous enzyme activity is preferably increased by mutation of the corresponding endogenous gene. Such mutations can either be generated randomly by means of classical methods such as, for instance, UV radiation or mutation-triggering chemicals, or else in a targeted manner by means of genetic-engineering methods such as deletion(s), insertion(s) and/or nucleotide exchange(s).

According to the invention, the gene expression is preferably intensified by increasing the number of genocopies. For this purpose, the gene or the genes is/are incorporated into a gene construct or into a vector that preferably contains the regulatory gene sequences associated with the genes, especially those that intensify the gene expression. Subsequently, a microorganism, preferably *Corynebacterium glutamicum*, is transformed with the corresponding gene constructs.

It was ascertained that the intensified expression of the valine biosynthesis gene ilvD from *Corynebacterium glutamicum*, which codes for the enzyme dihydroxy acid-dehydratase, produces L-valine in an improved manner. According to the invention, in addition to the intensified expression, of this gene, the intensified expression of the ilvBN genes that code for the enzyme acetohydroxy acid-synthase and of the ilvC gene that codes for the enzyme isomeroreductase also bring about improved formation of L-valine in *Corynebacterium glutamicum*. An additional improvement of the formation of L-valine is achieved through over-expression of all of the cited genes in *Corynebacterium glutamicum*. The genes or gene constructs can be present in the host organism either in plasmids with different numbers of genocopies or else they can be integrated and amplified in the chromosome.

An additional increase in the gene expression can be brought about—either as an alternative to or combined with an increase in the numbers of genocopies—by intensifying regulatory factors that have a positive effect on gene expression. For instance, regulatory elements can be intensified on the transcription level in that especially intensified transcription signals are employed. Moreover, the promoter and regulation region, which is located upstream from the structure gene, can be mutated. Expression cassettes incorporated upstream from the structure gene act in the same manner. By means of inducible promoters, it is additionally possible to increase the expression over the course of the fermentative formation of L-valine. Moreover, the translation can also be intensified, for example, by improving the stability of the m-RNA. Additionally, genes can be used that code for the corresponding enzyme having a high activity. Alternatively, an over-expression of the genes in question can be achieved by changing the medium composition and culture management. The person skilled in the art can find instructions on this, among others, in Martin et al. (Bio/Technology 5, 137-146 (1987)), in Guerrero et al. (Gene 138, 35-41 (1994)), in Tsuchiya and Morinaga (Bio/Technology 5, 428-430 (1988)), in Eikmanns et al. (Gene 102, 93-98 (1991)), in European patent specification EP 0,472,869, in U.S. Pat. No. 4,601,893, in Schwarzer and Pühler (Bio/Technology 9, 84-87 (1991)), in Reinscheid et al. (Applied and Environmental Microbiology 60, 126-132 (1994)), in LaBarre et al. (Journal of Bacteriology 175, 1001-1007 (1993)) and in the patent application WO 96/15246.

By the same token, all conceivable combinations of the above-mentioned measures can be used to intensify the gene expression.

Microorganisms that can be used in the process according to the invention can produce L-valine from glucose, sucrose, lactose, fructose, maltose, molasses, starch, cellulose or from glycerin and ethanol. These can be gram-positive bacteria, for instance, of the *Bacillus* genus or coryneform bacteria of the above-mentioned *Corynebacterium* genus or else *Arthrobacter*. As far as the *Corynebacterium* genus is concerned, special mention was already made of the *Corynebacterium glutamicum* species, which is known in specialized circles for its capability to form amino acids. This species includes wild-type strains such as, for example, B. *Corynebacterium glutamicum* ATCC13032, *Brevibacterium flavum* ATCC14067, *Brevibacterium lactofermentum* ATCC13869, *Brevibacterium thiogenitalis* ATCC19240, *Corynebacterium melassecola* ATCC17965 and others.

In order to isolate the gene ilvD from *Corynebacterium glutamicum* or other genes, first a gene bank is set up. How to set up gene banks is laid down in generally known text books and manuals. Examples of these are the text book by Winnacker: Gene und Klone, Eine Einführung in die Gentechnologie [Genes and clones: an introduction to genetic engineering] (published by Verlag Chemie, Weinheim, Germany, 1990) or the manual by Sambrook et al.: Molecular Cloning, A Laboratory Manual (Cold Spring Harbor Laboratory Press, 1989). A known gene bank is the *E. coli* K-12 strain W3110, which was set up by Kohara et al. (Cell 50, 495-508 (1987)) in λ-vectors. Bathe et al. (Molecular and General Genetics, 252: 255-265, 1996) describe a gene bank of *Corynebacterium glutamicum* ATCC13032, which was set up using the cosmid vector SuperCos I (Wahl et al., 1987, Proceedings of the National Academy of Sciences USA, 84: 2160-2164) in the *E. coli* K-12 NM554 (Raleigh et al., 1988, Nucleic Acids Research 16: 1563-1575). Plasmids such as pBR322 (Bolivar, Life Sciences, 25, 807-818 (1979)) or pUC19 (Norrander et al., 1983, Gene, 26: 101-106) can also be used to set up a gene bank of *Corynebacterium glutamicum* in *Escherichia coli*. Plasmids such as pJC1 (Cremer et al., Mol. Gen. Genet. (1990) 220: 3221-3229) or pECM2 (Jager et al., J. Bacteriol. (1992) 174: 5462-54465) can be used to produce a gene bank of *Corynebacterium glutamicum* in *Corynebacterium glutamicum*. Particularly suitable hosts are bacteria strains that are restriction-defective or recombination-defective. An example of this is the strain *Escherichia coli* DH5αmcr, which was described by Grant et al. (Proceedings of the National Academy of Sciences USA, 87 (1990) 4645-4649) or the strain *Corynebacterium glutamicum* R127, which was isolated by Liebl et al. (FEMS Lett. (1989) 65: 299-304).

The gene bank is subsequently incorporated into an indicator strain by means of transformation (Hanahan, Journal of Molecular Biology 166, 557-580, 1983) or by means of electroporation (Tauch et al., 1994, FEMS Microbiological Letters, 123: 343-347). The indicator strain is characterized by the fact that it has a mutation in the gene of interest that brings about a detectable phenotype, for example, an auxotrophy. The indicator strains or mutants can be obtained from published sources or strain collections or else, if necessary, can be produced by researchers themselves. Within the scope of the present invention, the *Corynebacterium glutamicum* mutant R127/7 was isolated, which is defective in the ilvD gene that codes for the dihydroxy acid-dehydratase. After transformation of the indicator strain such as, for example, the ilvD mutant R127/7, with a recombinant plasmid that carries the gene of interest such as, for instance, the ilvD gene, and after the expression thereof, the indicator strain becomes prototrophic in terms of the property in question such as, for example, its L-valine-requiring characteristics.

The gene or DNA fragment thus isolated can be characterized by the determination of the sequence such as described, for instance, by Sanger et al. (Proceedings of the National Academy of Sciences the United States of America, 74: 5463-5467, 1997). Subsequently, the degree of identity to known genes that are stored in databases such as, for example, the GenBank (Benson et al., 1998, Nucleic Acids Research, 26: 1-7), can be analyzed by means of published methods (Altschul et al., 1990, Journal of Molecular Biology 215: 403-410).

In this manner, the DNA sequence of *Corynebacterium glutamicum* that codes for the gene ilvD, which is an integral part of the present invention as SEQ ID NO 1. Furthermore, the amino acid sequences of the corresponding enzymes were derived from the present DNA sequence using the methods described above. In SEQ ID NO 2, the resultant amino acid sequence of the ilvD gene product, namely, dihydroxy acid-dehydratase, is prepared.

The thus characterized gene can be subsequently expressed either individually or else in combination with others in a suitable microorganism. A known method to express or over-express genes consists of amplifying them by means of plasmid vectors which can be additionally provided with expression signals. Examples of suitable plasmid vectors are those that can replicate in the corresponding microorganisms. The following vectors are possibilities in the case of *Corynebacterium glutamicum*: pEKEx1 (Eikmanns et al., Gene 102: 93-98 (1991)) or pZ8-1 (European patent specification no. 0,375,889) or pEKEx2 (Eikmanns et al., Microbiology 140: 1817-1828 (1994) or pECM2 (Jäger et al., Journal of Bacteriology 174 (16): 5462-5465 (1992)). Examples of such plasmids are pJC1ilvD, pECM3ilvBNCD and pJC1ilvBNCD. These plasmids are *Escherichia coli/Corynebacterium glutamicum* pendulum vectors that carry the gene ilvD or the gene ilvD together with the genes ilvB, ilvN and ilvC.

The inventors have also found that the intensification of the gene individually or in combination with the genes ilvB, ilvN, ilvC has an advantageous effect in those microorganisms that display a reduced synthesis of the amino acid L-isoleucine. This reduced synthesis can also be achieved through deletion of the ilvA gene that codes for the enzyme threonine dehydratase that is specific for L-isoleucine synthesis.

The deletion can also be carried out through targeted recombinant DNA techniques. By means of these methods, for example, the ilvA gene that codes for threonine dehydratase in the chromosome can be deleted. Suitable methods for this are described by Schafer et al. (Gene (1994) 145: 69-73) or by Link et al. (Journal of Bacteriology (1998) 179: 6228-6237). It is also possible to delete just parts of the gene or else the mutated fragments of the threonine dehydratase gene can be exchanged. Therefore, the deletion brings about a loss of the threonine dehydratase activity. An example of such a mutant is the *Corynebacterium glutamicum* strain ATCC 13032ΔilvA, which has a deletion in the ilvA gene.

The inventors have also found that the intensification of the genes ilvD, ilvB, ilvN and ilvC in another combination with the reduced synthesis of D-pantothenate, preferably in combination with further deletion of the ilvA gene, has an advantageous effect on the formation of L-valine in microorganisms, for example, by means of deletions in the panB gene and panC gene. The reduced D-pantothenate synthesis can be achieved by weakening or eliminating the corresponding biosynthesis enzymes or their activities. Examples of these are the enzymes ketopantoate hydroxymethyl transferase (EC 2.1.2.11), ketopantoate reductase, pantothenate ligase (EC 6.3.2.1) and aspartate decarboxylase (EC 4.1.1.11). Mutagenesis processes are a way to eliminate or weaken enzymes and their activities.

These include random processes that make use of chemical reagents such as, for instance, N-methyl-N-nitro-nitrosoguanidine or else UV irradiation to induce muta-genesis with a subsequent search of the desired microorganisms for their D-pantothenate-requiring properties. Processes to trigger mutation and to search for mutants are generally known and can be found, among other sources, in Miller (A Short Course in Bacterial Genetics, A Laboratory Manual and Handbook for *Escherichia coli* and Related Bacteria (Cold Spring Harbor Laboratory Press, 1992)) or in the publication titled "Manual of Methods for General Bacteriology" of the American Society for Bacteriology (Washington, D.C. U.S.A., 1981).

This also includes targeted recombinant DNA techniques. By means of these methods, for example, the genes panB, panC, panE and panD that code for the ketopantoate hydroxymethyl transferase, pantothenate ligase, ketopantoic acid reductase or aspartate decarboxylase can be deleted individually or else together in the chromosome. Suitable methods for this purpose are described by Schäfer et al. (Gene (1994) 145: 69-73) and by Link et al. (Journal of Bacteriology (1998) 179: 6228-6237). It is also possible to delete only parts of the genes or else to exchange mutated fragments of the ketopantoate hydroxymethyl transferase, pantothenate ligase, ketopantoic acid reductase and aspartate decarboxylase. Thus, deletion or exchange brings about a loss or a reduction of the enzyme activity in question. An example of such a mutant is the *Corynebacterium glutamicum* strain ATCC13032ΔpanBC, which carries a deletion in the panBC operon.

The microorganisms produced according to the invention can be cultivated either continuously or discontinuously in a batch process or else in a fed batch or repeated fed batch process for purposes of producing the L-valine. A compilation of the known cultivation methods is presented in the textbook by Chmiel (Bioprozesstechnik 1. Einführung in die Bioverfahrenstechnik [Bioprocess Technology, 1. Introduction to Bioprocess Technology] (Gustav Fischer Verlag, Stuttgart, 1991)) or in the textbook by Storhas (Bioreaktoren und periphere Einrichtungen [Bioreactors and Peripherals] (published by Vieweg Verlag, Braunschweig/Wiesbaden, Germany, 1994)).

The culture medium to be used has to appropriately meet the demands of the individual microorganisms. Descriptions of culture media for various microorganisms can be found in the publication titled "Manual of Methods for General Bacteriology" of the American Society for Bacteriology (Washington D.C., U.S.A., 1981). Sources of carbon can be sugars and carbohydrates such as glucose, sucrose, lactose, fructose, maltose, molasses, starch and cellulose, oils and fats such as, for instance, soy oil, sunflower oil, peanut oil and coconut fat, fatty acids such as, for example, palmitic acid, stearic acid and linoleic acid, alcohols such as, for example, glycerin and ethanol as well as organic acids such as, for instance, acetic acid. These substances can be employed either individually or in the form of a mixture. Sources of nitrogen can be organic compounds containing nitrogen such as peptones, yeast extract, meat extract, malt extract, corn-steep liquor, soybean meal and urea or else inorganic compounds such as ammonium sulfate, ammonium chloride, ammonium phosphate, ammonium carbonate and ammonium nitrate. The nitrogen sources can be used either individually or as in the form of a mixture. Potassium dihydrogen phosphate or dipotassium hydrogen phosphate or else the corresponding salts containing sodium can be used as the phosphorus source. The culture medium also has to contain salts of metals such as, for instance, magnesium sulfate or iron sulfate, which are needed for the growth. Finally, essential growth substances such as amino acids and vitamins can be employed in addition to the above-mentioned substances. The feedstocks cited can be added to the culture in the form of a one-time batch or else fed in a suitable manner during the cultivation.

In order to control the pH of the culture, alkaline compounds such as sodium hydroxide, potassium hydroxide and ammonia or else acidic compounds like phosphoric acid or sulfuric acid are employed in the appropriate manner. Antifoaming agents such as, for example, fatty acid-polyglycol ester, can be used to control foam formation. In order to maintain the stability of plasmids, suitable, selective-action substances can be added to the medium such as, for instance, antibiotics. To maintain aerobic conditions, oxygen or gas mixtures containing oxygen such as, for example, air, are fed into the culture. The temperature of the culture normally lies between 20° C. and 50° C. [68° F. and 122° F.], preferably between 25° C. and 45° C. [77° F. and 113° F.]. The culture is continued until a maximum quantity of L-valine has formed. This objective is normally achieved within 10 to 160 hours.

The concentration of L-valine formed can be determined using known methods (Jones and Gilligan (1983) Journal of Chromatography 266: 471-482).

The invention will be elaborated upon below on the basis of the following examples of embodiments.

EXAMPLE 1

Cloning, Sequencing and Expressing the ilvD Gene from *Corynebacterium glutamicum* that Codes for the Dihydroxy Acid-Dehydratase 1. Isolation of an ilvD Mutant of *Corynebacterium glutamicum*

The strain *Corynebacterium glutamicum* R127 (Haynes 1989, FEMS Microbiology Letters 61: 329-334) was mutated with N-methyl-N-nitro-N-nitrosoguanidine (Sambrook et al., Molecular Cloning. A laboratory manual (1989) Cold Spring Harbor Laboratory Press). For this purpose, 5 mL of a *Corynebacterium glutamicum* culture grown overnight was mixed with 250 µL of N-methyl-N-nitro-nitrosoguanidine (5 mg/mL of dimethyl formamide) and incubated for 30 minutes at 30° C. [86° F.] and at 200 rpm (Adelberg 1958, Journal of Bacteriology 76: 326). The cells were subsequently washed twice with sterile NaCl solution (0.9%). By means of replica plating on CGXII minimal medium plates with 15 g/L of agar (Keilhauer et al., Journal of Bacteriology 175: 5595-5603), mutants were isolated that only grew when L-valine, L-isoleucine and L-leucine were added (0.1 g/L of each).

The enzyme activity of the dihydroxy acid-dehydratase was determined in the raw extract of these mutants. For this purpose, the clones were cultivated in 60 mL of LB medium and centrifuged out in the exponential growth phase. The cell pellet was washed once with 0.05 M potassium phosphate buffer and resuspended in the same buffer. Cell digestion was achieved by means of a 10-minute ultrasound treatment (Branson-Sonifier W-250, manufactured by Branson Sonic Power Co., Danbury, Conn., United States). Subsequently, the cell fragments were separated out by a 30-minute centrifugation step at 13,000 rpm and at 4° C. [39.2° F.], and the supernatant was employed as the raw extract in the enzyme test. The reaction batch of the enzyme test contained 0.2 mL of 0.25 M tris/HCl, pH of 8, 0.05 mL of raw extract and 0.15 mL of 65 mM α,β-dihydroxy-β-methyl valerate. The test batches were incubated at 30° C. [86° F.]; after 10, 20 and 30 minutes, 200-µL samples were taken each time and their concentration of ketomethyl valerate was determined by means of HPLC analysis (Hara et al. 1985, Analytica Chimica Acta 172: 167-173). As can be seen in Table 1, the strain R127/7 does not display any dihydroxy acid-dehydratase activity, in contrast to which the isomeroreductase activity and the acetohydroxy acid-synthase activity are still present as additional enzymes of the synthesis of the branched-chain amino acids.

TABLE 1

Specific activities (µmol/min and mg of protein) of valine biosynthesis enzymes in *Corynebacterium glutamicum* strains.

| Strain | Dihydroxy acid-dehydratase | Isomeroreductase | Acetohydroxy acid-synthase |
|---|---|---|---|
| R127 | 0.003 | 0.05 | 0.07 |
| R127/7 | 0.000 | 0.06 | 0.09 |

2. Cloning of the ilvD Gene of *Corynebacterium glutamicum*

Figure 2:
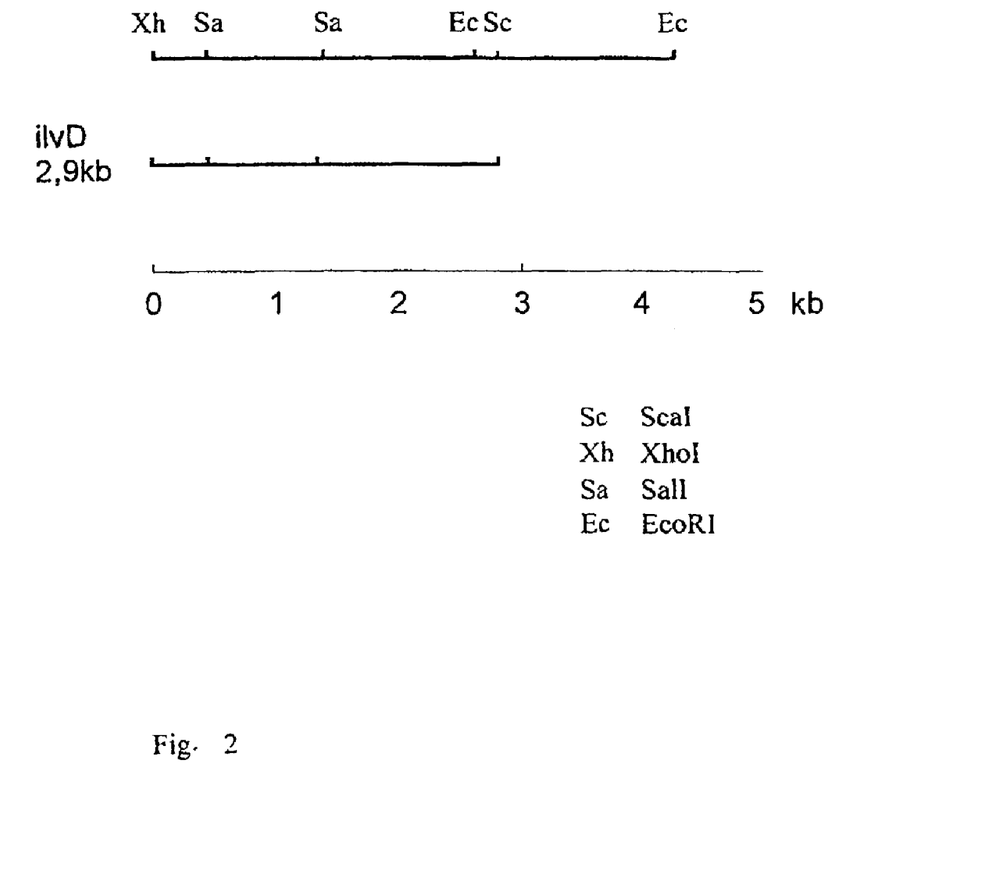
FIG. 2 shows a restriction fragment map of the 2.9 kb ScaI/XhoI DNA fragment containing ilvD from *Corynebacterium glutamicum*.

Chromosomal DNA from *Corynebacterium glutamicum* R127 was isolated as described by Schwarzer and Pühler (Bio/Technology 9 (1990) 84-87). It was then split with the restriction enzyme Sau3A (manufactured by Boehringer Mannheim, Germany) and separated out by means of sucrose-density-gradient centrifugation (Sambrook et al., Molecular cloning. A laboratory manual (1989) Cold Spring Harbor Laboratory Press). The fraction having the fragment size range from about 6 to 10 kb was employed for ligation with the vector pJC1 (Cremer et al., Molecular and General Genetics 220 (1990) 478-480). For this purpose, the vector pJC1 was linearized and dephosphorylated with BamHI. Five nanograms of this were ligated with 20 nanograms of the cited fraction of the chromosomal DNA, as a result of which the mutant R127/7 was transformed through electroporation (Haynes and Britz, FEMS Microbiology Letters 61 (1989) 329-334). The transformants were tested for their ability to grow on CGXII agar plates without the addition of branched-chain amino acids. Of the more than 5000 transformants tested, 8 clones grew on minimal medium plates following replica plating and two-day incubation at 30° C. [86° F.]. These clones were employed to make plasmid preparations as described by Schwarzer et al. (Bio/Technology (1990) 9: 84-87). Restriction analyses of the plasmid DNA revealed that all 8 clones contained the same plasmid, referred to below as pRV. The plasmid carries an insert of 4.3 kb and was tested by means of retransformation for its capacity to complement the ilvD mutant R127/7. Sub-cloning was utilized to delimit the range responsible for the complementation of the mutant R127/7 to a 2.9 ScaI/XhoI fragment (FIG. 2).

3. Sequencing of the ilvD Gene

The nucleic acid sequence of the 2.9 kb ScaI/XhoI fragments was determined by the dideoxy chain-termination method by Sanger et al. (Proceedings of the National Academy of Sciences of the United States of America (1977) 74: 5463-5467). An Auto-Read Sequencing Kit (Amersham Pharmacia Biotech, Uppsala, Sweden) was used for this. The gel-electrophoretic analysis was carried out with an automatic laser fluorescence sequencer (ALF) manufactured by Amersham Pharmacia Biotech (Uppsala, Sweden). The nucleotide sequence obtained was analyzed with the HUSAR program package (Release 4.0, EMBL, Cambridge, Great Britain). The nucleotide sequence is designated as ID SEQ NO 1. The analysis revealed an open reading frame of 1836 base pairs that was identified as ilvD gene and that codes for a polypeptide of 612 amino acids, which is designated as SEQ ID NO 2.

4. Expression of the ilvD Gene

The plasmid pRV was digested with the restriction enzymes ScaI and XhoI in accordance with the information provided by the manufacturer of the restriction enzymes (Roche, Boehringer Mannheim, Germany). Subsequently, the 2.9 kb ilvD fragment was isolated using ion-exchange columns (Quiagen, Hilden, Germany). The overhanging end of the XhoI section of the isolated fragment was filled up with Klenow polymerase. The vector pJC1 (Cremer et al., Mol. Gen. Genet. (1990) 220: 478-480) was PstI-sectioned, likewise treated with Klenow polymerase and subsequently the fragment and the vector were ligated. The ligation batch was employed to transform (Hanahan, Journal of Molecular Biology 166 (1983) 557-580) the *E. coli* strain DH5αmcr (Grant et al., Proceedings of the National Academy of Sciences of the United States of America, 87 (1990) 4645-4649). Using plasmid preparations of clones (Sambrook et al.: Molecular Cloning, A Laboratory Manual (1989) Cold Spring Harbor Laboratory Press), a clone was identified that contained the recombinant plasmid pJC1ilvD. This plasmid was utilized to transform *Corynebacterium glutamicum* ATCC13032 by means of electroporation, as described by Haynes et al. (1989, FEMS Microbiology Letters 61: 329-334). Subsequently, the dihydroxy acid-dehydratase activity coded by ilvD was determined on the basis of *Corynebacterium glutamicum* ATCC13032 pJC1 and *Corynebacterium glutamicum* ATCC13032pJC1ilvD. For this purpose, the clones were cultivated in 60 mL of LB medium and centrifuged out in the exponential growth phase. The cell pellet was washed once with 0.05 M potassium phosphate buffer and resuspended in the same buffer. Cell digestion was achieved by means of a 10-minute ultrasound treatment (Branson-Sonifier W-250, manufactured by Branson Sonic Power Co., Danbury, Conn., United States). Subsequently, the cell fragments were separated out by a 30-minute centrifugation step at 13,000 rpm and at 4° C. [39.2° F.], and the supernatant was employed as the raw extract in the enzyme test. The reaction batch of the enzyme test contained 0.2 mL of 0.25 M tris/HCl, pH of 8, 0.05 mL of raw extract and 0.15 mL of 65 mM α,β-dihydroxy-β-methyl valerate. The test batches were incubated at 30° C. [86° F.]; after 10, 20 and 30 minutes, 200-μL samples were taken each time and their concentration of ketomethyl valerate was determined by means of HPLC analysis (Hara et al. 1985, Analytica Chimica Acta 172: 167-173). As can be seen in Table 2, the strain *Corynebacterium glutamicum* ATCC13032 pJC1ilvD displays increased dihydroxy acid-dehydratase activity in comparison to the control strain.

TABLE 2

Specific activity (μmol/min and mg of protein) of the dihydroxy acid-dehydratase in *Corynebacterium glutamicum* ATCC13032.

| Plasmid | Dihydroxy acid-dehydratase |
|---|---|
| pJC1 | 0.008 |
| pJC1ilvD | 0.050 |

EXAMPLE 2

Construction of an ilvA Deletion Mutant of *Corynebacterium glutamicum*

The internal deletion of the ilvA gene of *Corynebacterium glutamicum* ATCC13032 was carried out by means of the system described by Schäfer et al. (Gene 145: 69-73 (1994)) for gene exchange. In order to construct the inactivation vector pK19mobsacBΔilvA, first an internal 241 bp BglII fragment was removed from the ilvA gene present on an EcoRI fragment in the vector pBM21 (Möckel et al. 1994, Molecular Microbiology 13: 833-842). For this purpose, the vector was sectioned with BglII, and religated after separation of the ilvA-internal BglII fragment by means of agarose-gel electrophoresis. Subsequently, the incomplete gene was isolated from the vector as an EcoRI fragment and ligated in the vector pK10mobsacB (Schäfer 1994, Gene 145: 69-73) that had been linearized with EcoRI. The inactivation vector pK19mobsacBΔilvA thus obtained was introduced into the *E. coli* strain S 17-1 by means of transformation (Hanahan 1983, Journal of Molecular Biology 166, 557-580) and transferred to *Corynebacterium glutamicum* ATCC13032 via conjugation (Schafer et al. 1990, Journal of Bacteriology 172: 1663-1666). Kanamycin-resistant clones of *Corynebacterium glutamicum* were obtained in which the inactivation vector was integrated in the genome. In order to select the excision of the vector, kanamycin-resistant clones were plated on LB medium containing sucrose (Sambrook et al., Molecular Cloning, A Laboratory Manual (1989) Cold Spring Harbor Laboratory Press) with 15 g/L of agar, 2% glucose/10% sucrose and colonies were obtained that had once again lost the vector through a second recombination event (Jager et al. 1992, Journal of Bacteriology 174: 5462-5465). By means of inoculation on minimal medium plates (medium CGXII with 15 g/L of agar (Keilhauer et al., Journal of Bacteriology 175 (1993) 5595-5603)) with and without 2 mM L-isoleucine or with and without 50 μg/mL of kanamycin, 36 clones were isolated that were kanamycin-sensitive due to excision of the vector and that were isoleucine-auxotrophic and in which the incomplete ilvA gene (ΔilvA allele) was now present in the genome. A strain was designated as ATCC13032ΔilvA and further employed.

EXAMPLE 3

Cloning of the Genes of the Pantothenate Biosynthesis panB and panC from *Corynebacterium glutamicum*

Cloning of the Operon

Figure 3:
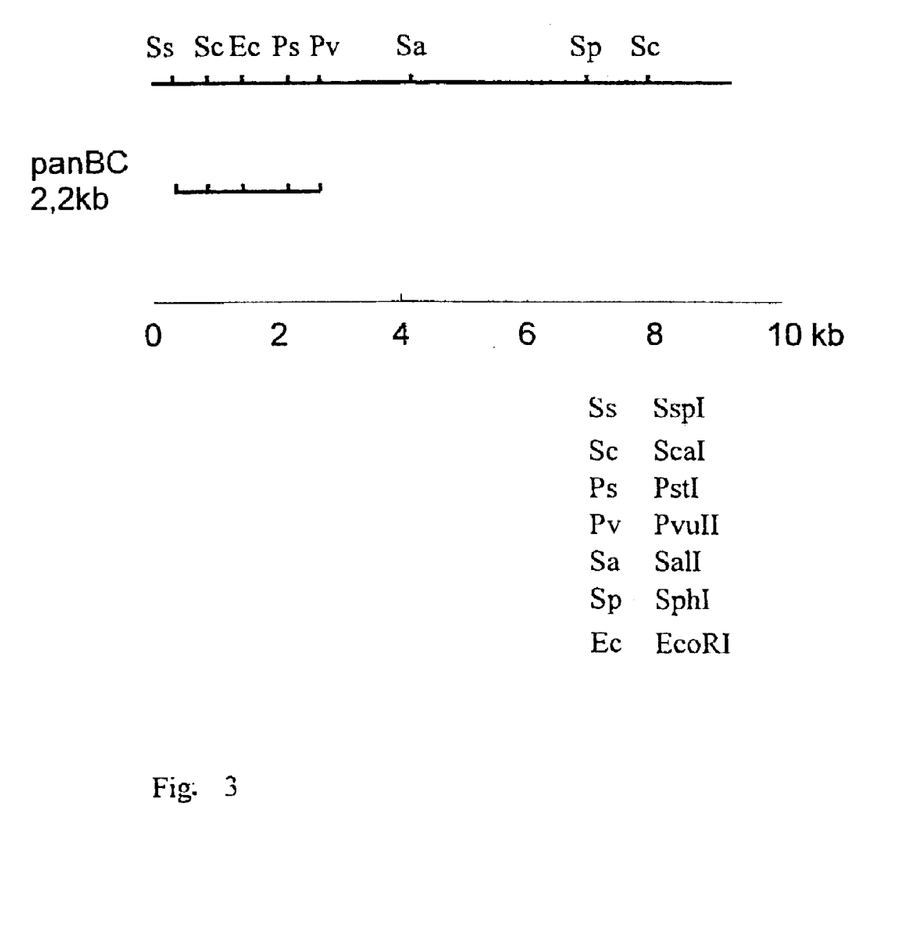
FIG. 3 shows a restriction fragment map of the 2,2 kb DNA fragment containing panBC from *Corynebacterium glutamicum*.

Chromosomal DNA from *Corynebacterium glutamicum* ATCC13032 was isolated and sectioned with the restriction endonuclease Sau3A. Following gel-electrophoresis separation, DNA fragments within a size range from 3' to 7 kb or from 9 to 20 kb were extracted and subsequently ligated in the singular BamHI section site of the vector pBR322. Colonies having inserts were isolated on the basis of their sensitivity to tetracycline after inoculation on LB plates with 10 μg/mL of tetracycline. Using plasmid preparations (Sambrook et al.: Molecular Cloning, A Laboratory Manual (1989) Cold Spring Harbor Laboratory Press) of pooled clones, 8 plasmid pools were isolated, each of which contained 400 plasmids having an insert size of 9 to 20 kb and 9 plasmid pools, each containing 500 plasmids having an insert size of 3 to 7 kb. The *E. coli* panB mutant SJ2 (Cronan et al. 1982, J. Bacteriol. 149: 916-922) was transformed with this gene bank by means of electroporation (Wehrmann et al. 1994, Microbiology 140: 3349-3356). The transformation batches were plated directly on CGXII medium (J. Bacteriol. (1993) 175: 5595-5603). Plasmid DNA was isolated (Sambrook et al. 1989) from clones that were capable of growing without supplementation with pantothenate and retransformation was employed to obtain 8 clones whose D-pantothenate-requiring properties were confirmed. A restriction mapping was carried out with the 8 clones. One of the vectors examined, referred to below as pUR1, contained an insert of 9.3 kb (FIG. 3). The transformation of the *E. coli* panC mutant DV39 (Vallari et al. 1985, J. Bacteriol. 164: 136-142) showed that the vector pUR1 was likewise capable of complementing the panC defect of this mutant. A 2.2-kb fragment of the insert of pUR1 was sequenced according to the dideoxy chain-termination method by Sanger et al. (Proceedings of the National Academy of Sciences of the United States of America (1977) 74: 5463-5467). The gel-electrophoresis analysis was carried out using an automatic laser fluorescence sequencer (A.L.F.) manufactured by Amersham Pharmacia Biotech (Uppsala, Sweden). The nucleotide sequence obtained was analyzed with the HUSAR program package (Release 4.0, EMBL, Cambridge, Great Britain). The nucleotide sequence is designated as ID SEQ NO 3. The analysis revealed the identification of two open reading frames. One open reading frame encompasses 813 base pairs and exhibits a high level of homology to the already known panB genes from other organisms. The panB gene from *C. glutamicum* codes for a polypeptide of 271 amino acids (see SEQ ID NO 4). The second open reading frame encompasses 837 base pairs and exhibits a high level of homology to the already known panC genes from other organisms. The panC gene from *C. glutamicum* codes for a polypeptide of 279 amino acids (see SEQ ID NO 5).

EXAMPLE 4

Construction of a panBC Deletion Mutant from *Corynebacterium glutamicum*

The system for gene exchange described by Schafer et al. (Gene 145: 69-73 (1994)) was used for the genomic panBC fragment of *Corynebacterium glutamicum* ATCC13032 as well as of *Corynebacterium glutamicum* ATCC1303ΔilvA. In order to construct the deletion vector pK19mobsacBΔpanBC, first the 3.95-kb SspI/SalI fragment with panBC was ligated with pUC18 which had been previously SamI/SalI-sectioned. Subsequently, a 1293-bp EcoRV/NruI fragment was removed from the overlapping area of the panBC gene by means of restriction digestion and religation. In order to allow the subcloning into pK19mobsacB, the deleted panBC area was amplified in pUC18 with the two primers 5'-GAGAACTTAATCGAGCAACACCCCTG, 5'-GCGCCACGCCTAGCCTTGGC-CCTCAA and the polymerase chain reaction (PCR) in order to obtain a 0.5-kb ΔpanBC that carries a SalI or EcoRI section site at the ends. The PCR was carried out according to Sambrook et al. (Molecular Cloning, A Laboratory Manual (1989) Cold Spring Harbor Laboratory Press) at an annealing temperature of 55° C. [131° F.]. The fragment thus obtained was ligated with the vector pK19mobsac that had been previously EcoRI/SalI-sectioned and treated with alkaline phosphatase. The resultant inactivation vector pK19mobsacBΔpanBC was introduced into the *Escherichia coli* strain S 17-1 (Hanahan (1983) J. Mol. Biol. 166: 557-580) by means of transformation and then transferred to *Corynebacterium glutamicum* ATCC13032 (Schafer et al. (1990) J. Bacteriol. 172: 1663-1666) via conjugation. Kanamycin-resistant clones of *Corynebacterium glutamicum* were obtained in which the inactivation vector was integrated in the genome. In order to select for the excision of the vector, kanamycin-resistant clones were plated on LB medium containing sucrose (Sambrook et al., Molecular Cloning, A Laboratory Manual (1989) Cold Spring Harbor Laboratory Press) with 15 g/L of agar, 2% glucose/10% sucrose and colonies were obtained that had once again lost the vector through a second recombination event (Jäger et al. 1992, Journal of Bacteriology 174: 5462-5465). By means of inoculation on minimal medium plates (medium CGXII with 15 g/L of agar (Keilhauer et al., Journal of Bacteriology 175 (1993) 5595-5603) with and without 2 mM L-isoleucine or with and without 50 µg/mL of kanamycin, 36 clones were isolated that were kanamycin-sensitive due to excision of the vector and that were isoleucine-auxotrophic and in which the incomplete ilvA gene (ΔilvA alleles) was now present in the genome. A strain was designated as ATCC13032ΔpanBC. As was described in detail in the example, the panBC deletion was also introduced into ATCC13032ΔilvA so as to yield the strain ATCC13032ΔilvAΔpanBC.

EXAMPLE 5

Expression of the Genes ilvD, ilvBN and ilvC in *Corynebacterium glutamicum*

The genes of acetohydroxy acid-synthase (ilvBN) and of isomeroreductase (ilvC) (Cordes et al. 1992, Gene 112: 113-116 and Keilhauer et al. 1993, Journal of Bacteriology 175: 5595-5603) and of dihydroxy acid-dehydratase (ilvD) (Example 1) were cloned for expression into the vector pECM3. The vector pECM3 is a derivative of pECM2 (Jäger et al. 1992, Journal of Bacteriology 174 (16): 5462-5465), which was created by deletion of the approximately 1 kbp-long BamHI/BglII DNA fragment that carries the kanamycin resistance gene.

In the vector pKK5 (Cordes et al. 1992, Gene 112: 113-116), the ilvBNC genes were already present in a cloned state in the vector pJC1 (Cremer et al. 1990, Molecular and General Genetics 220: 478-480). From this, a 5.7-kb XbaI-ilvBNC fragment was isolated and, together with a 3.1-kb XbaI fragment of the vector pRV, it was introduced into the vector pECM3 that had been linearized with XbaI. In this process, the ligation batch was transformed into the *E. coli* strain DH5αmcr. The plasmid pECM3ilvBNCD was obtained from one clone.

By means of electroporation (Haynes 1989, FEMS Microbiology Letters 61: 329-334) and selection for chloramphenicol resistance (3 µg/mL), the plasmid pECM3ilvBNCD was introduced into the strain ATCC13032ΔilvA and the strain ATCC13032ΔilvA/pECM3ilvBNCD was obtained.

EXAMPLE 6

Production of L-Valine with Various Strains of *Corynebacterium glutamicum*

In order to examine their valine formation, the strains listed in Table 4 were pre-cultivated in 60 mL of brain heart infusion medium (Difco Laboratories, Detroit, Mich., United States) for 14 hours at 30° C. [86° F.]. Subsequently, the cells were washed once with 0.9% NaCl solution (w/v) and, with this suspension, 60 mL of CGXII medium were inoculated in such a way that the OD600 amounted to 0.5 The medium was identical to the medium described by Keilhauer et al. (Journal of Bacteriology (1993) 175: 5595-5603). For the cultivation of the ΔilvA strains, the medium additionally contained 250 mg/L of L-isoleucine. This is shown in Table 3.

TABLE 3

| Composition of the medium CGXII. | |
|---|---|
| Component | Concentration |
| $(NH_4)_2SO_4$ | 20 g/L |
| urea | 5 g/L |
| $KH_2PO_4$ | 1 g/L |
| $K_2HPO_4$ | 1 g/L |
| $Mg_2O_4 \cdot 7H_2O$ | 0.25 g/L |
| 3-morpholinopropane sulfonic acid | 42 g/L |
| $CaCl_2$ | 10 mg/L |
| $FeSO_4 \cdot 7H_2O$ | 10 mg/L |
| $MnSO_4 \cdot H_2O$ | 10 mg/L |
| $ZnSO_4 \cdot 7H_2O$ | 1 mg/L |
| $CuSO_4$ | 0.2 mg/L |
| $NiCl_2 \cdot 6H_2O$ | 0.02 mg/L |
| biotin (pH 7) | 0.2 mg/L |
| glucose | 40 g/L |
| protocatechuic acid | 0.03 mg/L |

After 48 hours of cultivation, samples were taken, the cells were centrifuged out and the supernatant underwent sterile filtration. The L-valine concentration of the supernatant was determined by means of high-pressure liquid chromatography with integrated pre-column derivatization of the amino acid with o-phthdialdehyde as described by Jones and Gilligan (J. Chromatogr. 266 (1983) 471-482). The results are presented in Table 4.

TABLE 4

L-valine production with various *Corynebacterium glutamicum* strains.

| C. glutamicum | L-valine (mM) |
|---|---|
| ATCC 13032 | 0.5 |
| ATCC 13032 pJC1ilvD | 2.2 |
| ATCC 13032 pJC1ilvBNC | 20.0 |
| ATCC 13032 pJC1ilvBNCD | 26.2 |
| ATCC 13032 ΔilvA | 2.7 |
| ATCC 13032 ΔilvA pJC1ilvD | 7.0 |
| ATCC 13032 ΔilvA pJC1ilvBNCD | 28.5 |
| ATCC 13032 ΔpanBC | 8.2 |
| ATCC 13032 ΔilvAΔpanBC | 31.1 |
| ATCC 13032 ΔilvAΔpanBC pJC1ilvBNCD | 72.7 |

The invention claimed is:

1. A microorganism transformed with a nucleotide sequence encoding dihydroxy acid dehydratase (ilvD), nucleotide sequences encoding acetohydroxy acid synthase and isomeroreductase (ilvBNC) or both ilvD and ilvBNC, in which microorganism the activity of one or more enzymes that are specifically involved in the synthesis of D-pantothenate is reduced or eliminated,
wherein said one or more enzymes are selected from the group consisting of ketopantoate hydroxymethyl transferase (panB), pantothenate ligase (panC), ketopantoic acid reductase (panE) and aspartate decarboxylase (panD) and said activity of said one or more enzymes is reduced or eliminated as a result of deletion of all or a part of the nucleotide sequence encoding said enzyme in said microorganism and
wherein said microorganism is a *Corynebacterium* species and said nucleotide sequence encoding ilvD comprises the portion of SEQ ID NO: 1 encoding ilvD.

2. The transformed microorganism according to claim 1 in which the activity of the enzyme ketopantoate hydroxymethyl transferase (panB), the enzyme pantothenate ligase (panC) or both panB and panC is reduced or eliminated as a result of deletion of all or a part of the nucleotide sequence encoding said enzyme in said microorganism.

3. The transformed microorganism according to claim 1 in which the activity of the enzyme threonine dehydratase (ilvA) is reduced or eliminated as a result of deletion of all or a part of the nucleotide sequence encoding said ilvA in said microorganism.

4. The transformed microorganism according to claim 1 wherein said microorganism is *Corynebacterium glutamicum*.

5. A method for the production of L-valine comprising the step of culturing a microorganism transformed with a nucleotide sequence encoding dihydroxy acid dehydratase (ilvD) and nucleotide sequences encoding acetohydroxy acid synthase and isomeroreductase (ilvBNC), under conditions wherein said microorganism produces L-valine, wherein said microorganism is a *Corynebacterium* species and said nucleotide sequence encoding ilvD comprises the portion of SEQ ID NO: 1 encoding ilvD.

6. The method of claim 5 wherein the activity of threonine dehydratase (ilvA) in said microorganism is reduced or eliminated as a result of deletion of all or a part of the nucleotide sequence encoding said ilvA in said microorganism.

7. The method of claim 5 wherein the activity of at least one enzyme in said microorganism selected from the group consisting of ketopantoate hydroxymethyl transferase (panB), pantothenate ligase (panC), ketopantoic acid reductase (panE) and aspartate decarboxylase (panD) is reduced or eliminated as a result of deletion of all or a part of the nucleotide sequence encoding said enzyme in said microorganism.

8. The method of claim 7 wherein said at least one enzyme is panB or panC.

9. The method of claim 8 wherein said at least one enzyme is panB and panC.

10. The method of claim 6 wherein the activity of at least one enzyme in said microorganism selected from the group consisting of ketopantoate hydroxymethyl transferase (panB), pantothenate ligase (panC), ketopantoic acid reductase (panE) and aspartate decarboxylase (panD) is reduced or eliminated as a result of deletion of all or a part of the nucleotide sequence encoding said enzyme in said microorganism.

11. The method of claim 10 wherein said at least one enzyme is panB or panC.

12. The method of claim 11 wherein said at least one enzyme is panE and panC.

13. The method of claim 5 wherein said *Corynebacterium* species is *Corynebacterium glutamicum*.

14. A method for the production of L-valine comprising the step of culturing a microorganism in which the activity of dihydroxy acid dehydratase (ilvD) is increased by increased expression of the ilvD nucleotide sequence encoding ilvD, under conditions wherein said microorganism produces L-valine, wherein said microorganism is a *Corynebacterium* species and said nucleotide sequence encoding ilvD comprises the portion of SEQ ID NO: 1 encoding ilvD.

15. The method of claim 14 wherein the acetohydroxy acid synthase and isomeroreductase (ilvBNC) activity of said microorganism is increased as a result of mutation of the endogenous gene encoding said ilvBN or ilvC or both.

16. The method of claim 14 wherein said microorganism is transformed with a nucleotide sequence encoding acetohydroxy acid synthase and isomeroreductase (ilvBNC).

17. The method of claim 14 wherein the activity of threonine dehydratase (ilvA) in said microorganism is reduced or eliminated as a result of deletion of all or a part of the nucleotide sequence encoding said ilvA in said microorganism.

18. The method of claim 15 wherein the activity of threonine dehydratase (ilvA) in said microorganism is reduced or eliminated as a result of deletion of all or a part of the nucleotide sequence encoding said ilvA in said microorganism.

19. The method of claim 18 wherein the activity of at least one enzyme in said microorganism selected from the group consisting of ketopantoate hydroxymethyl transferase (panB), pantothenate ligase (panC), ketopantoic acid reductase (panE) and aspartate decarboxylase (panD) is reduced or eliminated as a result of deletion of all or a part of the nucleotide sequence encoding said enzyme in said microorganism.

20. The method of claim 19 wherein said at least one enzyme is panB or panC.

21. The method of claim 20 wherein said at least one enzyme is panB and panC.

22. The method of claim 14 wherein said *Corynebacterium* species is *Corynebacterium glutamicum*.

23. The microorganism of claim 1, wherein said microorganism is transformed with a nucleotide sequence encoding ilvD or nucleotide sequences encoding both ilvD and ilvBNC.

* * * * *